United States Patent [19]

Kloss

[11] Patent Number: 5,045,470
[45] Date of Patent: Sep. 3, 1991

[54] DEVICE FOR SUBMERGED CULTURE OF TISSUE CELLS

[75] Inventor: Gerd Kloss, Kolbermoor, Fed. Rep. of Germany

[73] Assignee: Stawag, Schlieren, Switzerland

[21] Appl. No.: 455,381

[22] PCT Filed: Apr. 4, 1989

[86] PCT No.: PCT/CH89/00067
§ 371 Date: Feb. 5, 1989
§ 102(e) Date: Feb. 5, 1989

[87] PCT Pub. No.: WO89/09814
PCT Pub. Date: Oct. 19, 1989

[30] Foreign Application Priority Data
Apr. 5, 1988 [CH] Switzerland ............ 1244/88

[51] Int. Cl.⁵ .................... C12M 3/00; C12N 5/00
[52] U.S. Cl. .................... 435/284; 435/813; 435/819; 435/286; 435/240.25; 435/240.46; 422/224
[58] Field of Search ......... 435/286, 313, 284, 314, 435/315, 813, 819, 240.25, 240.46; 422/224

[56] References Cited
U.S. PATENT DOCUMENTS

| | | | |
|---|---|---|---|
| 2,121,458 | 6/1938 | Vogelbusch | 435/315 |
| 4,379,846 | 4/1983 | Shkidchenko et al. | 435/315 |
| 4,494,878 | 1/1985 | Rainey, Jr. | 422/224 |

FOREIGN PATENT DOCUMENTS

| | | | |
|---|---|---|---|
| 0095804 | 12/1983 | European Pat. Off. | |
| 3313081 | 10/1984 | Fed. Rep. of Germany | |
| 765295 | 6/1934 | France | |
| 0729239 | 4/1980 | U.S.S.R. | 435/313 |

OTHER PUBLICATIONS
Composite Sciences Inc. in Chemical Eng., 81(6), p. 80.

Primary Examiner—David L. Lacey
Assistant Examiner—William K. Y. Chan
Attorney, Agent, or Firm—Herbert Dubno

[57] ABSTRACT

An apparatus for submerged culture of tissue cells in which gas is supplied to the culture medium in an upright sterilizable container through a rotating hollow shaft having a plurality of sets of radially extending blades from which the gas is discharged only along upper surfaces of the blades within a cage formed by vertically spaced hollow baffle plates connected by hollow posts through which gas is supplied to the baffle plates and is charged into the nutrient medium through porous parts of the plates.

5 Claims, 1 Drawing Sheet

DEVICE FOR SUBMERGED CULTURE OF TISSUE CELLS

CROSS REFERENCE TO RELATED APPLICATIONS

This application is a national phase application of PCT/CH89/00067 filed Apr. 4, 1989, and based upon a Swiss National Application 1244/88-6 filed Apr. 5, 1988, under the International Convention.

FIELD OF THE INVENTION

The invention relates to a device for submerged culture of vegetable, animal and human tissue cells within a closed chamber, consisting of a container that can be sterilized and is equipped with a centrally disposed, rotatable hollow shaft having one or more stirring elements and baffles arranged one above the other.

BACKGROUND OF THE INVENTION

For the submerged culture of tissue cells the standard stirrers and mixers used in the cultivation of microorganisms have proved to be unsuitable due to the shearing forces which were generated during their operation. Particularly when cultivating human cell lines, the strong mechanical movements lead to inadmissible damage to the cells. One has therefore carried out the exchange of nutrients and gases by the so-called airlift method whereby the aerating medium took care of the necessary mixing by means of passing through perforated plates. Also a combination of pneumatic and mechanical mixing was tried.

In particular, EP-A-0 095 804 describes a method for the submerged culture of tissue cells whereby a stirrer operating at a relatively low speed provides for a thorough mixing of nutrients and air, while a sintered plate arranged on the bottom of the container provides of the gassing. This known device is disadvantageous because the gas transfer to and from the cell is insufficent since gassing within a restricted space can take place only from the bottom of the container. The relatively slow motion of the stirrer prevents a sufficient aeration in the area of the container walls and in the upper zone of the container.

OBJECT OF THE INVENTION

It is an object of the invention to provide a device that permits an optimal gassing in a cultivation container and avoids damage to the cells.

SUMMARY OF THE INVENTION

The device, according to the invention, has characterized in baffle plates arranged between each pair of stirring elements and equipped with a gas-impermeable part and a gas-permeable part.

This device has the advantage that the gassing can be effected with high intensity on different levels up to the surface of the liquid, in spite of the slow-moving stirrer. The element-type construction of the stirring elements on the hollow shaft permits their assembly in containers of different dimensions, depending upon the kind of cells to be cultivated. Across the hollow stirring elements an optimal gassing is thus assured on each level without the danger of cells being damaged due to shear forces generated by a high-speed stirrer.

It is particularly advantageous to make the upper part of the stirring elements of high-grade stainless steel sheet, which has proved to be particularly suitable. The gas apertures may be round or of any other suitable shape.

It is advantageous to provide the upper part of the stirring elements as a porous body whereas the lower part is closed. On the other hand the entire stirring element may consist of a porous material.

As a porous material sintered metal, ceramics and synthetic material are suitable. It synthetic material is used, it must be thermally stable enough so as to withstand several sterilizations at temperatures of about 130 centigrades without becoming damaged.

For particular cell cultivations, it has proved to be suitable to provide the gas-permeable part of the baffle plates with a semipermeable diaphragm. Such a diaphragm permits, besides the gas transfer, also the supply of nutrient medium.

In addition it has proved to be advantageous to arrange the baffle plates between a pair of stirring element within a removable baffle plate cage. The baffle plate cage may be cleaned separately and pre-sterilized if required. In this manner slow-moving stirrers having a great surface area and provided with gas passages on their upper side may rotate within a baffle plate cage.

It is of advantage if the baffle plates, too, consist of a hollow body and can be used for reinforcing the gassing if required. In such a case the baffle plates consist, like the stirring element, of a gas-impermeable and of a gas-permeable hollow body.

BRILF DESCRIPTION OF THE DRAWING

The invention will now be explained in detial with reference to the accompanying drawing wherein.

SPECIFIC DESCRIPTION

Figure 1:
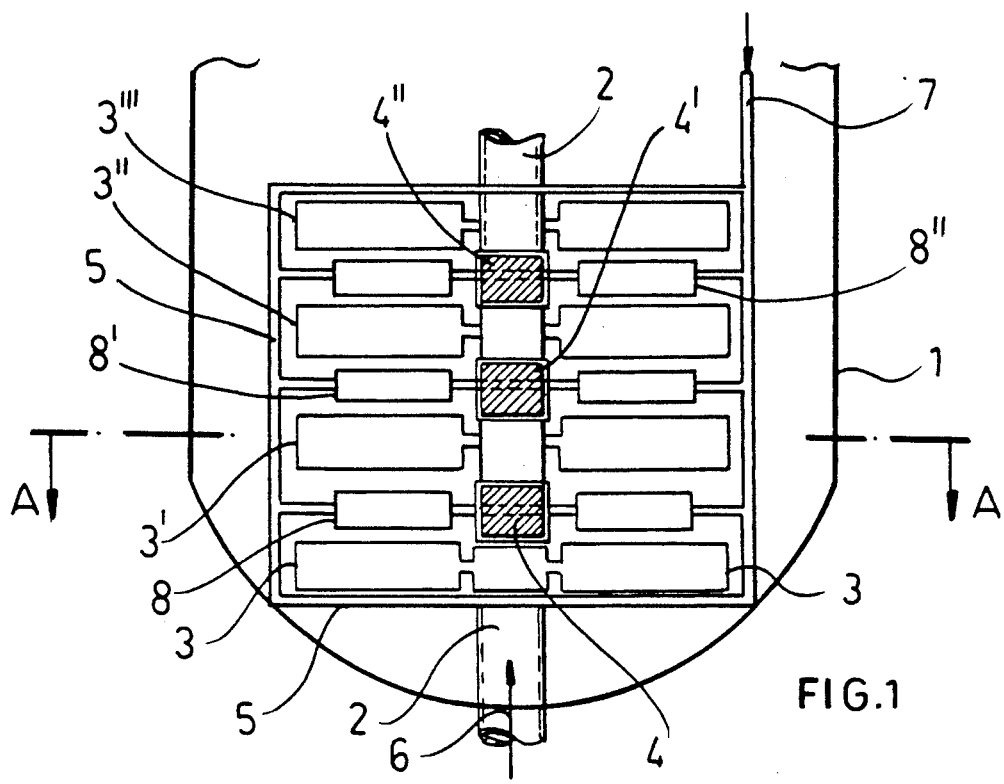
FIG. 1 is a diagrammatic sectional view which illustrates an arrangement of the stirring elements according to the invention together with a baffle plate cage in the lower part of a container.
Figure 2:
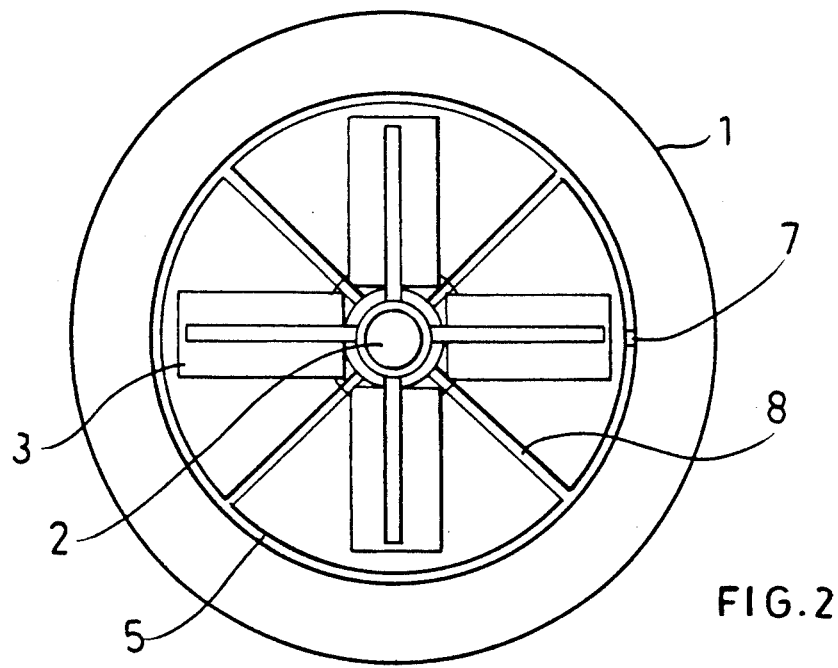
FIG. 2 is a cross-section through the container taken along line A—A in FIG. 1.

FIG. 1 shows the lower part of a container 1 with a hollow shaft 2. The hollow shaft, in its lower part, leads through the container wall in known manner, seals being provided at this location. Hollow shaft 2 is connected at its lower end to an electric motor, not represented, and to a gas supply conduit 6. On hollow shaft 2, pairs of stirring elements 3, 3', 3" and 3'" are disposed, separated from each other by spacers 4, 4', 4". A baffle plate cage 5 is arranged in such a manner within container 1 that it encloses all stirring elements 3 to 3'" as well as baffle plates 8, 8'and 8". Baffle plate cage 5 has a conduit 7 for the supply of a pressurized gas. FIG. 2 illustrates how the pairs of stirring elements 3 etc. are arranged within baffle plate cage 5. Instead of a stirring element having four flaps one with two blades may be used. Within stirring element 3 air conduits 9 are provided which are connected to hollow shaft 2. Baffle plates 8 etc., too, may be made hollow and connected to hollow baffle plate cage 5 which in turn is connected to conduit 7 for the gas supply.

Figure 3:
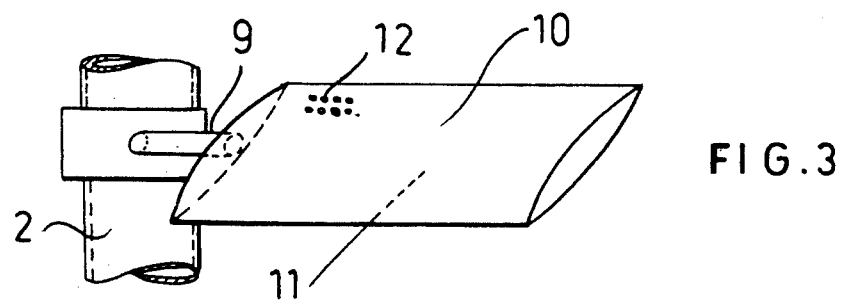
FIG. 3 is a perspective view showing details of a stirring element.

In FIG. 3 stirring element 3 is shown in a perspective view, it is composed of a gas-permeable upper part 10 with gas outlet apertures 12, and of a closed lower part 11. In the interior of stirring element 3, air conduit 9 is shown in dotted lines, connected to hollow shaft 2. In operation, container 1 is provided with a nutrient medium and tissue cells. Hollow shaft 2 is rotated at a speed of 30 rpm at the most, preferably at 5 to 15 rpm. Simultaneously pressurized air is supplied via gas supply conduit 6 and hollow shaft 2 to hollow stirring elements 3. Preferably the gas outlet is at the upper side of the stirring elements 3. The stirring effect is assured by the baffle plates 8 arranged between the stirring elements 3 within baffle plate cage 5. For an increased need of gas, pressurized air may be supplied to the baffle plates 8 via conduit 7 and hollow baffle plate cage 5, the baffle plates 8 comprising in this case outlet apertures for the gas, too. As can be seen from FIG. 1, the baffle plates 8, etc. are located between the sets of blades at the levels of the spacers 4 and are held by vertical posts.

Instead of an upper side 10 of the blades 3 provided with holes, perforations or pores a semipermeable diaphragm (membrane) may be provided. The supply of medium may then be effected through hollow shaft 2 into the stirring elements 3. In this way the stirring elements 3 may be used for an intensive metabolic process. Baffle plates 8, too, may be provided with these diaphragms for intensifying this metabolic process. In this case the medium is supplied via hollow baffle plate cage 5. The device according to the invention is particularly suitable for cultivating cells and cell lines sensitive to shear stresses and is largely independent of the shape of the container due to the alternative arrangement of hollow stirring elements and baffle plates. Any number of stirring elements may be arranged one on top of the other in a simple manner, depending upon the requirements. An additional advantage resides in the fact that the medium supply may be effected simultaneously with the gas supply via the gas supply conduit.

The device is not only suitable for cultivating tissue cells but also for cultivating microorganisms of all kinds, in particular those that are sensitive to shear stresses.

I claim:

1. An apparatus for submerged culturing of tissue cells, comprising:
   an upright sterilizable container;
   a rotatable vertical hollow shaft extending centrally in said container;
   a plurality of sets of radially extending blades spaced apart on said shaft and communicating with said hollow shaft, each of said blades being permeable to gas only along an upper surface thereof whereby gas introduced into said shaft flows out of said upper surfaces of said blades into a culture medium in said container, each of said sets comprising at least one pair of said blades, said blades having gas-impermeable lower surfaces;
   spacers between said sets along said shaft;
   means for feeding said gas to said hollow shaft; and
   a cage in said container surrounding said shaft and said sets of blades said cage comprising:
      a plurality of vertically spaced hollow baffle plates each disposed between two of said sets,
      hollow posts outwardly of said blades attached to said plates and communicating with said plates,
      means for feeding gas to said hollow posts, and
      gas-permeable means on said plates for discharging gas into said medium.

2. The apparatus defined in claim 1 wherein said upper surfaces of said blades, comprise perforated sheets.

3. The apparatus defined in claim 1 wherein said upper surfaces of said blades comprise a porous sintered material.

4. The apparatus defined in claim 1 wherein said upper surfaces of said blades comprise a semipermeable membrane.

5. The apparatus defined in claim 1 wherein said gas-permeable means on said baffle plates are semipermeable membranes.

* * * * *